July 9, 1940. W. I. JOHNSTON Plant Pat. 410
ROSE PLANT
Filed March 8, 1940
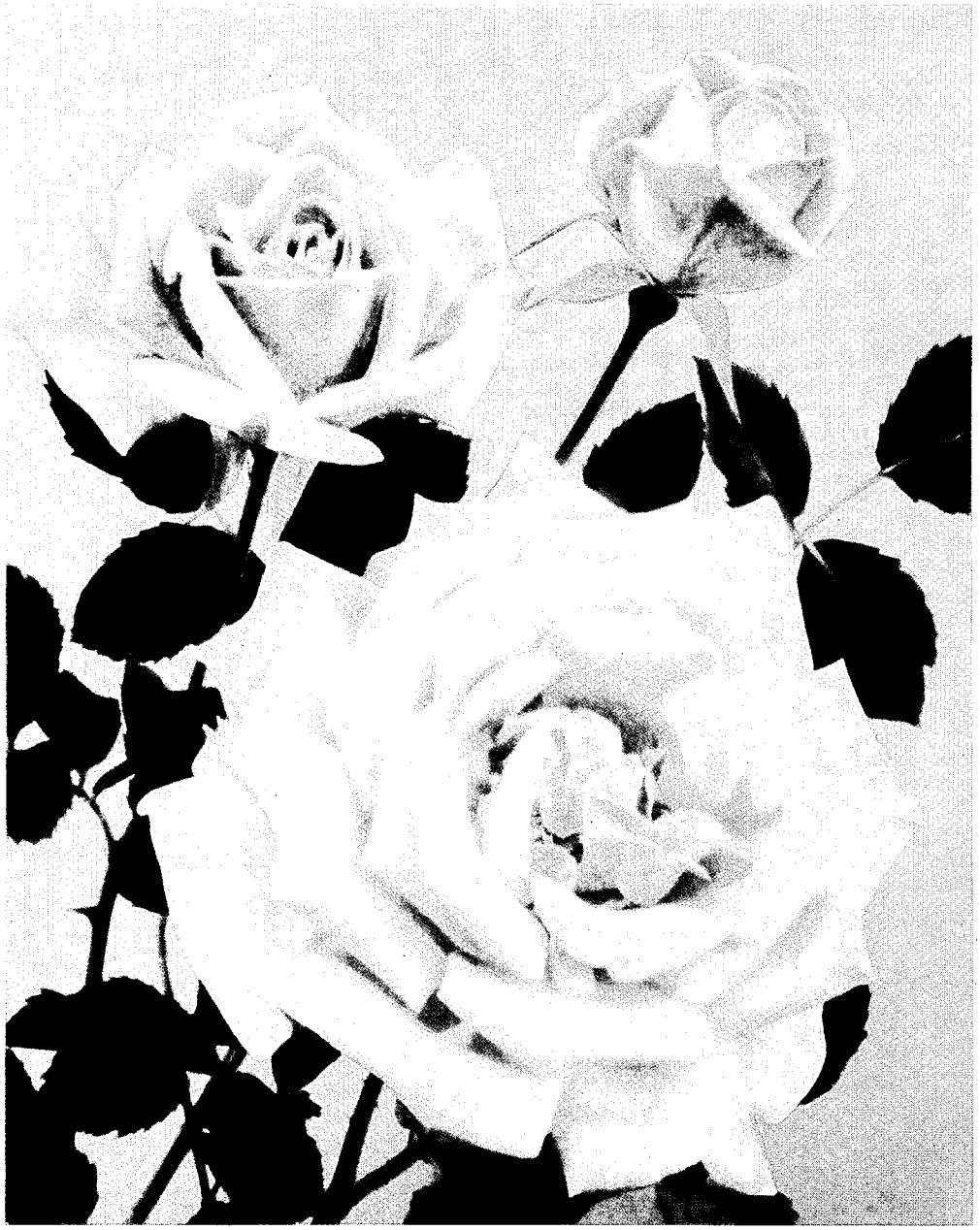
Inventor
W. I. Johnston
By Robb & Robb
attorneys Patented July 9, 1940

Plant Pat. 410

UNITED STATES PATENT OFFICE

410

ROSE PLANT

Walter Irwin Johnston, Portadown, Ireland, assignor to Jackson & Perkins Company, Newark, N. Y.

Application March 8, 1940, Serial No. 323,015

1 Claim. (Cl. 47—61)

The present invention relates to a new and distinct variety of rose plant, evidenced by its vigorous and very free blooming habit, the unusually attractive color combination of the flowers, and the contrasting coloring of the foliage of the plant.

This new rose, grown from a seedling of the cross of Mrs. Henry Morse, known to be one of the backbones, so to speak, of the pink planting in many rose gardens, with an unnamed seedling of desirable characteristics.

More specifically, the novelty of the coloring characteristics of this new variety, resides in the Eosine Pink outer petals and the Begonia Rose color in the center of the flower; the Empire Yellow color at the base of the inside of the petals and the suffusion of this color through the Eosine Pink color of the inside of the petals; and the color between Tosine Pink and Spinel Red on the reverse of the petals.

As regards the foliage, the rose is characterized as to novelty by the Dark Mineral Red coloring of the edges and the Cress Green center of the upper side of the young foliage, together with the Mineral Red color of the under side traced with light Cress Green veining.

In the illustration of the rose, these coloring features are shown as nearly as possible for an artist to depict in detail, though it is to be understood that exactness in this respect is not claimed. However, such illustration, together with the following detailed description, is believed to suffice for purposes of this disclosure, all color terminology used being according to Ridgway's Color Standard.

Parentage: Seedling.
*Seed parent.*—Mrs. Henry Morse.
*Pollen parent.*—Unnamed seedling.

Classification: Botanic and commercial—Hybrid tea.

*Flower*

(Observations made in fields and gardens of Jackson & Perkins Company, Newark, New York, in the morning of September 8, 1939.)

Blooming habit: Recurrent—Continuous.

Bud:
*Size.*—Medium.
*Form.*—Ovoid. It is not affected by wet or hot weather.
*Color.*—When sepals first divide—Rose Doree, Plate 1. When petals begin to unfurl—Begonia Rose, Plate 1. When half blown: inside of petals—between Begonia Rose, Plate 1, and Deep Rose Pink, Plate 12, lower third suffused with Empire Yellow, Plate 4; reverse of petals—Eosine Pink, Plate 1, suffused with Empire Yellow, Plate 4.
*Sepals.*—Branched, slight "hood" above bud. Curl back when bud half blown.
*Calyx.*—*Shape*—funnel. *Size*—broad. *Aspect*—smooth.
*Peduncle.*—*Length*—long. *Aspect*—prickly. *Color*—Light Cress Green, plate 31, shaded with Corinthian Red, Plate 27. *Strength*—stiff, erect, heavy.
*Opening.*—Bud opens well. Is not affected by adverse conditions.

Bloom:
*Size.*—Large. Average size when fully expanded—4½-5 inches.
*Borne.*—Several together.
*Stems.*—Medium length, strong.
*Form.*—When first open—high center. Permanence—retains its form to the end.
*Petalage.*—Double (full but open center). Number of petals under normal conditions—45.
*Color.*—Center of flower—Begonia Rose, Plate 1. Outer petals—Eosine Pink, Plate 1. Base of petals (aiglet)—Empire Yellow, Plate 4. Inside of petals—Eosine Pink, Plate 1, suffused partway up with Empire Yellow, Plate 4. Reverse of petals—Between Eosine Pink, Plate 1, and Spinel Pink, Plate 26. General tonality from a distance—Eosine Pink, Plate 1.
*Discoloration.*—General tonality at end of first day—Eosine Pink, Plate 1. Second day—between Eosine Pink, Plate 1, and Deep Rose Pink, Plate 12. Third day—Deep Rose Pink, Plate 12.

Petals:
*Texture.*—Thick. Is not affected by wet or hot weather.
*Appearance.*—Inside—velvety. Outside—satiny.
*Form.*—Oval.
*Arrangement.*—Imbricated (regularly arranged shingle-like). Petaloids in center—few, small.
*Persistence.*—Drop off cleanly.
*Fragrance.*—Slight. *Nature*—tea (average hybrid tea scent).
*Lasting quality.*—On the plant and as cut flower—long.

Genital organs:
*Stamens, anthers.*—Small, many. Color—Light Cadmium, Plate 4. Arrangement—regular around styles.
*Stamens, filaments (threads).*—Medium length. *Color*—Xanthine Orange, Plate 3.
*Pollen.*—Apricot Yellow, Plate 4.
*Styles.*—Bunched; medium length, thin.
*Stigmas.*—Light Cadmium, Plate 4.
*Ovaries.*—All enclosed in calyx.

*Plant*

Form: Bush.
Growth: Vigorous.
Foliage: 3–5 leaflets.
*Size.*—Medium.
*Quantity.*—Normal.
*Color.*—*New foliage*: upper side—Dark Mineral Red, Plate 27, edges; center, Cress Green, plate 31; under side—Mineral Red, Plate 27, with veining of Light Cress Green, Plate 31. *Old foliage*: Upper side—Yew Green, Plate 31. Under side—Cress Green, Plate 31.
*Shape.*—Oval pointed.
*Texture.*—Upper side—leathery. Under side—smooth. Ribs and veins—ordinary.
*Edge.*—Serrated (saw toothed).
*Serration.*—Single; small.
*Rachis.*—Cress Green, Plate 31. Under side—smooth.
*Stipules.*—Medium length; bearded.
*Disease resistance.*—Resistant.

Wood:
*New wood.*—*Color*—Light Cress Green, Plate 31. *Bark*—smooth.
*Old Wood.*—*Color*—Cress Green, Plate 31. *Bark*—smooth.

Thorns (divided into thorns, pricles and short needles):
*Thorns.*—On main stalks from base and on laterals from stalk—many. *Form*—narrow base; hooked downward. *Color when young*—Cinnamon Brown, Plate 15. *Position*—irregular.
*Prickles.*—Green.

Asexual reproduction of this new rose shows that the noted distinctive features are fixed.

I claim:

A new and distinct variety of rose plant, characterized as to novelty by the vigorous and very free blooming habit and the combination coloring in the different stages of development of the flowers and foliage thereof, substantially as shown and described.

WALTER IRWIN JOHNSTON.